(12) United States Patent
Shows

(10) Patent No.: US 7,497,032 B2
(45) Date of Patent: Mar. 3, 2009

(54) FOOT PAIN-RELIEVING ARTICLES AND METHOD THEREOF

(76) Inventor: Michael D. Shows, 26532 Montebello Pl., Mission Viejo, CA (US) 82691

( * ) Notice: Subject to any disclaimer, the term of this patent is extended or adjusted under 35 U.S.C. 154(b) by 383 days.

(21) Appl. No.: 11/364,281

(22) Filed: Feb. 28, 2006

(65) Prior Publication Data

US 2006/0143941 A1 Jul. 6, 2006

Related U.S. Application Data

(63) Continuation-in-part of application No. 10/637,232, filed on Aug. 11, 2003, now Pat. No. 7,017,283.

(51) Int. Cl.
*A43B 7/02* (2006.01)
*A43B 7/06* (2006.01)
(52) U.S. Cl. ................. 36/2.6; 36/3 B; 36/3 A
(58) Field of Classification Search ............ 36/2.6, 36/3 B, 3 A, 3 R
See application file for complete search history.

(56) References Cited

U.S. PATENT DOCUMENTS

| | | | | | |
|---|---|---|---|---|---|
| 3,685,176 | A | * | 8/1972 | Rudy | 36/71 |
| 5,195,254 | A | * | 3/1993 | Tyng | 36/3 R |
| 5,375,430 | A | * | 12/1994 | Siegel | 62/259.3 |
| 5,806,208 | A | * | 9/1998 | French | 36/28 |
| 5,918,381 | A | * | 7/1999 | Landry | 36/3 B |
| 7,186,957 | B2 | * | 3/2007 | Martin | 219/529 |
| 2002/0050074 | A1 | * | 5/2002 | Ricco et al. | 36/3 R |

* cited by examiner

*Primary Examiner*—Ted Kavanaugh
(74) *Attorney, Agent, or Firm*—Veronica-Adele R. Cao; Weiss & Moy, P.C.

(57) ABSTRACT

Articles that provide foot pain-relief for wearers of shoes and methods are disclosed. Foot pain relief by cooling or heating of footwear is provided by footwear comprising a length of tubing coupled to and along at least a portion of the shoe insole and an aperture for the release of gas from a compressed gas cylinder into the tubing. The shoe is recharged as needed to provide continuous cooling or heating of a foot.

15 Claims, 2 Drawing Sheets

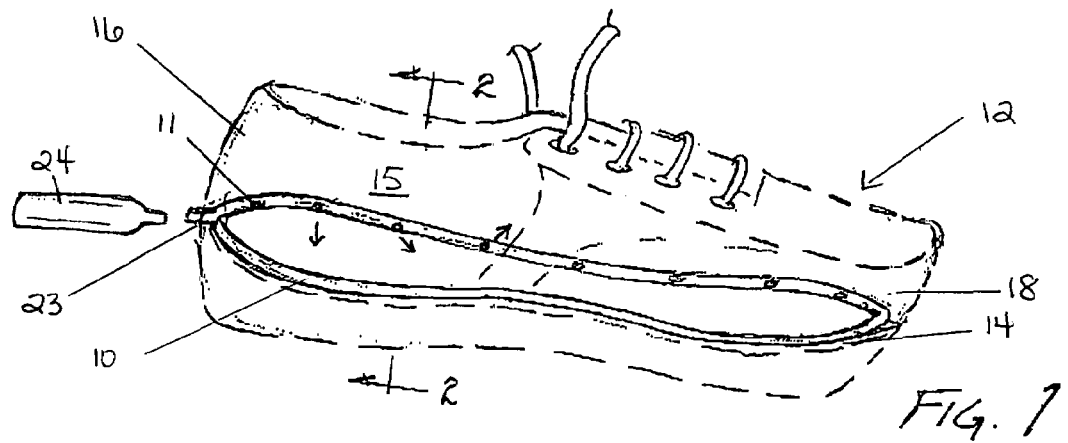
FIG. 1
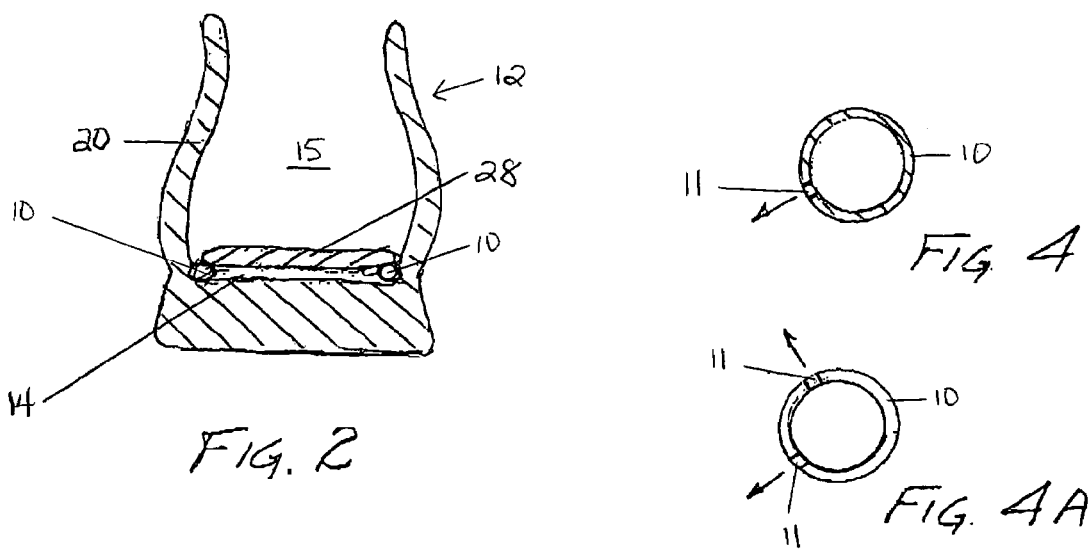
FIG. 2
FIG. 4
FIG. 4A
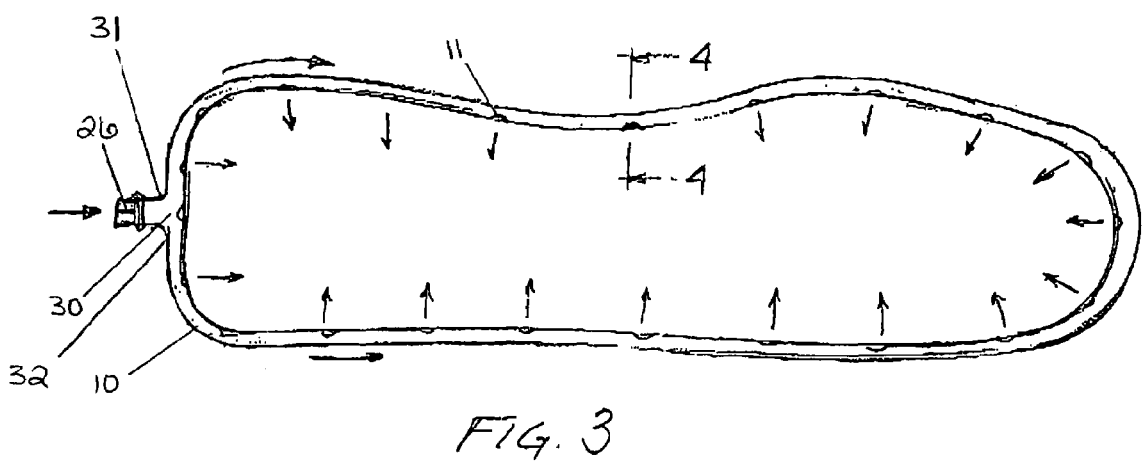
FIG. 3

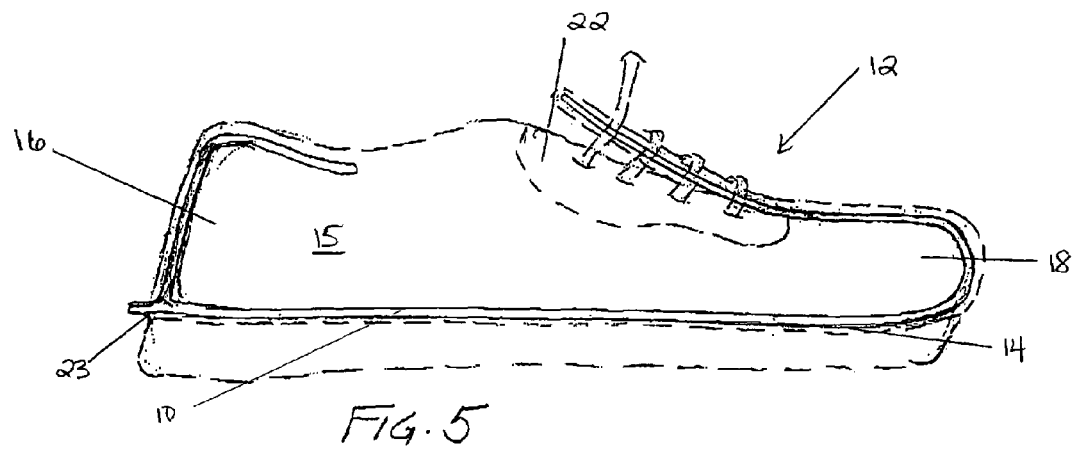
FIG. 5
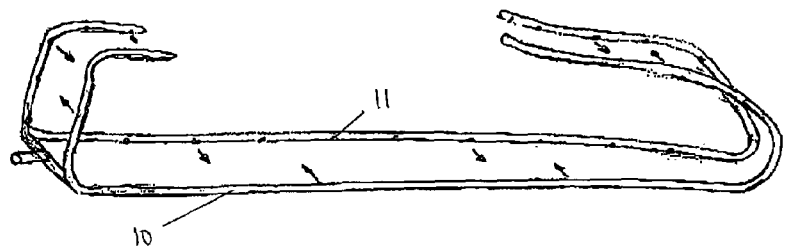
FIG. 6
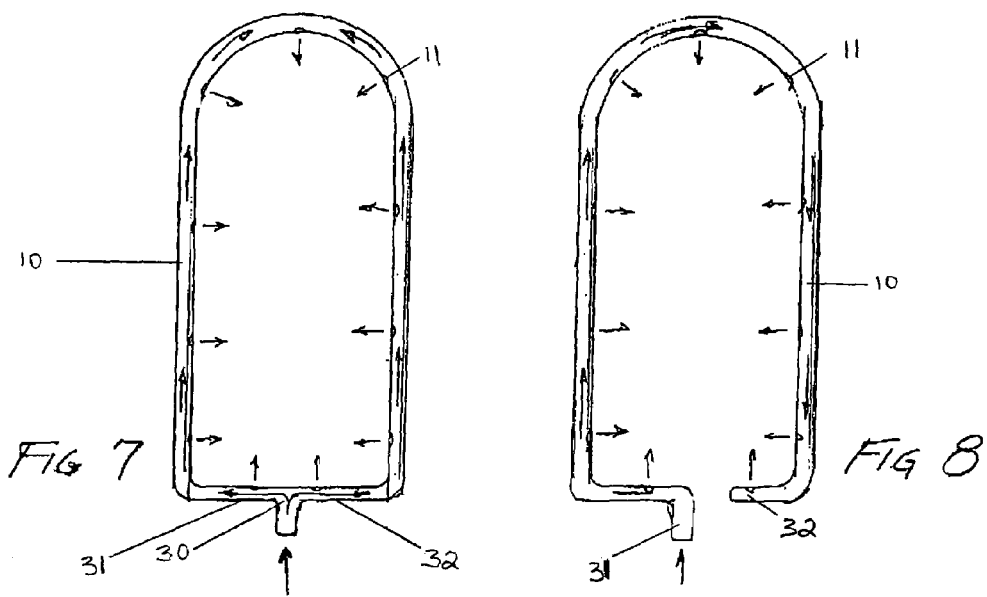
FIG 7
FIG 8

US 7,497,032 B2

FOOT PAIN-RELIEVING ARTICLES AND METHOD THEREOF

CROSS REFERENCE TO RELATED APPLICATION

This application is a continuation in part of application U.S. Ser. No. 10/637,232, filed Aug. 11, 2003 now U.S. Pat. No. 7,017,283 in the name of the applicant of this application.

FIELD OF THE INVENTION

This invention relates generally to foot pain-relief and more particularly to articles that provide foot pain-relief, articles for footwear and methods thereof.

BACKGROUND OF THE INVENTION

In the past, numerous articles were used for providing foot pain-relief. Typically, such articles were incorporated into the shape of footwear, such as a specific kind of molding to support arches of a foot in a shoe. Other articles were provided as inner sole inserts that were also specifically molded to provide foot support for a wearer of a shoe.

More recently, foot support has been achieved by the use of a liquid filled bladder (see French, U.S. Pat. No. 5,806,208). The liquid provides massaging action by way of special rib designs and valves, which direct flow of the liquid. In addition, in French, U.S. Pat. No. 5,806,208 replaceable liquids can be placed in the bladder to provide for cooling and warming of a specific shoe that is fitted with the bladder. French's shoe with a bladder U.S. Pat. No. 5,806,208 generally comprises an integral sole portion of the shoe that fits as an integral insole of the shoe and integral fingers extending from the integral sole portion. Also, the cooling and warming liquids are preferably introduced by means of a supply port so that the user can change or add liquid to the bladder. Re-introduction of the cooling or warming liquid is necessary for achieving cooling or warming in the shoe. Alternatively, placing the entire shoe structure into a cooler for cooling in the shoe or a microwave oven (or other heating source) for warming in the shoe achieves the same result.

It is desirable to provide means for cooling or warming shoes that do not depend on refilling a shoe with a liquid as provided for in French, U.S. Pat. No. 5,806,208) or that do not depend on placing the entire shoe into a cooler for cooling the shoe or into a heat source such as a microwave oven for warming of the shoe. Current devices and methods for achieving such means are not available.

For the foregoing reason, there is a need to provide improved articles that provide foot pain-relief for wearers of shoes and methods thereof. This invention provides foot pain-relief articles that use gases to warm or cool the feet of wearers of shoes.

SUMMARY OF THE INVENTION

Accordingly, it is an object of this invention to provide improved articles that provide foot pain-relief for wearers of shoes.

It is a further object of this invention to provide improved articles that provide foot pain-relief for shoe wearers, which use gases to warm or cool the feet of wearers of shoes.

It is yet a still further object of this invention to provide improved articles that provide foot pain-relief for wearers of shoes that may be integral or removable from shoes.

It is a further object of this invention to provide methods for providing foot pain-relief for wearers of shoes.

PREFERRED EMBODIMENTS OF THE INVENTION

In accordance with one embodiment of this invention, a foot pain-relief article for footwear is disclosed. The foot pain-relief article comprises, in combination a footwear product, a length of tubing coupled to and extending along an insole of the footwear product, and a source of a gas fluid adapted to be introduced through an aperture in a portion of the footwear product into the tubing and adapted to be activated by a person for internally altering a temperature of the footwear product.

In accordance with a second embodiment, a method for providing foot pain-relief for a footwear product is disclosed. The method comprises the steps of providing a footwear product having a length of tubing coupled to and extending along at least a periphery of an insole of the footwear product, and providing a source of a gas fluid adapted to be introduced through an aperture in a rear portion of the footwear product into the tubing and adapted to be activated by a person for internally altering the temperature of the footwear product.

The foregoing and other objects, features, and advantages of the invention will be apparent from the following, more detailed description of the preferred embodiments of the invention, as illustrated in the accompanying drawings.

BRIEF DESCRIPTION OF THE DRAWINGS

FIG. 1 is a perspective view of a shoe with a length of tubing coupled to and extending along a periphery of the shoe insole, which either warms or cools a foot according to the invention. A rear portion of the shoe has an opening for receiving a compressed gas cylinder in the heel of the shoe FIG. 2 is a cross-sectional view of the shoe of FIG. 1, taken along line 2-2 showing the length of tubing positioned between the shoe insole and a removable insert.

FIG. 3 is a top view of the length of tubing of the shoe of FIG. 1. Gas is shown entering the tubing and dispersing through the weep holes defined by the tubing.

FIG. 4 is a cross-sectional view of the tubing of FIG. 3, taken along line 4-4. Gas is shown dispersing through one weep hole.

FIG. 4a is a cross sectional view of the tubing of FIG. 3, taken along line 4-4. Gas is shown dispersing through two weep holes positioned at different angles.

FIG. 5 is a perspective view of a shoe (shown in phantom lines) with a length of tubing coupled to and extending along the shoe insole, the heel, the toe, the upper, and the tongue of the shoe.

FIG. 6 is a perspective view of the tubing of FIG. 5;

FIG. 7 is top view of the tubing of FIG. 1. A first end of the tubing and a second end of the tubing meet to form a substantially T-shaped junction and a spike is coupled to the tubing proximate the substantially T-shaped junction so that gas fluid flows substantially bidirectionally along the length of tubing.

FIG. 8 is a top view of the tubing of FIG. 1. A spike is coupled proximate a first end of the tubing so that the gas fluid flows substantially unidirectionally along the length of tubing.

DESCRIPTION OF THE INVENTION

FIGS. 1-9 refer to the preferred embodiment of the present invention. Together they show a foot pain-relief article for a footwear product. The article may either be integral to the shoe or may be inserted into the shoe separately.

Referring to FIG. 1-4a and FIGS. 7-8, a length of tubing 10 is coupled to and along a periphery of an insole 14 of a shoe 12. Preferably, the tubing 10 is located between the shoe insole 14 and a removable insert 28 (see FIG. 2). It should be clearly understood however that further substantial benefit may be derived from use of the invention with a shoe that does not have an insert and with a shoe having an insert that is permanently coupled to the insole 14 of the shoe 12. It should also be clearly understood that further substantial benefit may be derived from the tubing being coupled to and along a substantially center portion of the insole 14.

A gas is released when a compressed gas cylinder 24 (see FIG. 1) is pierced by a spike 26 (see FIG. 3) coupled to a portion of the tubing 10. Preferably, a heel 16 of the shoe 12 defines an aperture 23 and the spike 26 is preferably located within the aperture 23. While this is preferred, it should be clearly understood that further substantial benefit may be derived from the aperture 23 and spike 26 being located in a different area of the shoe 12 or from the spike 26 protruding from the shoe 12.

The release of gas from the compressed gas cylinder 24 results in cooling or heating of the shoe inner 15. As shown in FIGS. 1, 3, 4, and 4a, the tubing 10 preferably defines a plurality of weep holes 11 (or dispersion holes) for dispersing the gas toward the shoe inner 15. The weep holes 11 may be positioned at uniform angles (see FIG. 3) along the tubing 10 or at alternative angles (see FIGS. 1 and 4a) along the tubing 10 to allow for multidirectional dispersion of the gas within the shoe inner 15. While it is preferred that the tubing 10 have a plurality of weep holes 11, it should be clearly understood that further substantial benefit may nevertheless be derived from tubing 10 that does not have any weep holes 11.

The shoe 12 may be recharged with the gas as needed to continue cooling or heating the shoe 12. Any gas that is non-flammable and non-toxic may be used; however, it should be clearly understood that substantial benefit may be derived from any kind of non-flammable and non-toxic gas that is capable of providing either a cooling or heating effect. For cooling, carbon dioxide is a preferred gas in the compressed gas cylinder 24.

Referring now to FIGS. 5 and 6, the tubing 10 may also extend along a portion of the heel 16, a portion of the toe 18, a portion of the shoe upper 20, and/or a portion of the tongue 22 of the shoe 12. The gas would disperse through the weep holes into these additional areas, thereby heating or cooling these additional areas of the shoe 12.

Referring to FIG. 7, a first end 31 and a second end 32 of the tubing 10 meet to form a substantially T-shaped junction 30. The spike 26 is then coupled to the tubing 10 proximate the substantially T-shaped junction 30 so that the gas flows substantially bidirectionally from the substantially T-shaped junction 30 and then along the length of tubing 10. On the other hand, as shown in FIG. 8, the spike 26 may be coupled proximate the first end 31 of the tubing 10 so that the gas flows substantially unidirectionally along the length of tubing 10.

While the invention has been particularly shown and described with reference to preferred embodiments thereof, it will be understood by those skilled in the art that the foregoing and other changes in form and details may be made therein without departing from the spirit and scope of the invention. For example, a compressed gas cylinder comprising a valve and an inlet spout may be used to provide cooling gas into the tubing. The compressed gas cylinder may be introduced into the tubing of the shoe from an aperture in the sole of the shoe. As a further example, the tubing may branch out several times while passing throughout the areas of the shoe. The gas would then flow through each of the branches of the tubing.

I claim:

1. A foot pain-relief article for a footwear product comprising, in combination:
    a footwear product;
    an aperture in a portion of said footwear product;
    a length of tubing coupled to and extending along an insole of said footwear product;
    a plurality of weep holes along said length of tubing;
    a source of a gas fluid adapted to be introduced through said aperture into said tubing and adapted to be activated by a person, wherein said source of gas fluid is a compressed gas cylinder coupled to said footwear product; and
    gas fluid from said compressed gas cylinder for internally altering a temperature of said footwear product; wherein said gas fluid is dispersed through said weep holes toward an inner portion of said footwear product.

2. The foot pain-relief article for a footwear product according to claim 1 wherein said aperture being defined by a rear portion of said footwear product.

3. The foot pain-relief article for a footwear product according to claim 1 wherein said gas fluid being a cooling gas fluid to thereby internally cool said footwear product and cool a foot of a user of said footwear product.

4. The foot pain-relief article for a footwear product according to claim 1 wherein said gas fluid being a heating gas fluid to thereby internally heat said footwear product and heat a foot of a user of said footwear product.

5. The foot pain-relief article for a footwear product according to claim 1 wherein said length of tubing being coupled to and along a periphery of said insole.

6. The foot pain-relief article for a footwear product according to claim 1 wherein said tubing further extending along at least one of a portion of a heel, a portion of a toe, a portion of an upper, and a portion of a tongue of said footwear product.

7. The cooling foot pain-relief article according to claim 6 wherein said length of tubing defining a plurality of weep holes for dispersing said gas fluid toward at least one of a portion of said insole, a portion of said heel, a portion of said toe, a portion of said upper, and a portion of said tongue of said footwear product.

8. The cooling foot pain-relief article for a footwear product according to claim 1 further comprising a spike, said spike located within said aperture and coupled to a portion of said tubing for piercing said compressed gas cylinder containing said gas fluid to release said gas fluid into said tubing.

9. The cooling foot pain-relief article for a footwear product according to claim 8 wherein a first end of said tubing and a second end of said tubing meet to form a substantially T-shaped junction and wherein said spike being coupled to said tubing proximate said substantially T-shaped junction so that said gas fluid flows substantially bidirectionally along said length of tubing.

10. The foot pain-relief article for a footwear product according to claim 1 wherein the gas fluid is non-flammable.

11. A method for providing foot pain-relief for a footwear product comprising the steps of:
    providing a footwear product having a length of tubing coupled to and extending along at least a periphery of an insole of said footwear product;
    providing an aperture in a rear portion of said footwear product;

providing a source of a gas fluid adapted to be introduced through said aperture into said tubing and adapted to be activated by a person;

providing said source of a gas fluid as a compressed gas cylinder coupled to said footwear product;

providing a gas fluid from said compressed gas cylinder for internally altering a temperature of said footwear product;

providing a plurality of weep holes defined by said tubing; and dispersing said gas fluid through said weep holes toward an inner portion of said footwear product.

12. The foot pain-relief article for a footwear product according to claim 11 wherein said gas fluid being a cooling gas fluid to thereby internally cool said footwear product and cool a foot of a user of said footwear product.

13. The foot pain-relief article for a footwear product according to claim 11 wherein said gas fluid being a heating gas fluid to thereby internally heat said footwear product and heat a foot of a user of said footwear product.

14. The foot pain-relief article for a footwear product according to claim 11 wherein said gas fluid is non-flammable.

15. The method of claim 11 further comprising the steps of:

providing a spike coupled to a portion of said tubing, said spike being located within said aperture in said rear portion of said footwear product;

piercing said compressed gas cylinder with said spike to release said gas fluid contained within said compressed gas cylinder into said tubing.

* * * * *